United States Patent [19]
Andersen

[11] 4,188,989
[45] Feb. 19, 1980

[54] FLUID COLLECTION RECEPTACLE

[75] Inventor: Erik Andersen, Haarley, Denmark

[73] Assignee: G. D. Searle & Co., Skokie, Ill.

[21] Appl. No.: 935,229

[22] Filed: Aug. 21, 1978

Related U.S. Application Data

[63] Continuation of Ser. No. 716,308, Aug. 20, 1976, abandoned.

[51] Int. Cl.² .................................................. B65D 31/14
[52] U.S. Cl. .......................................... 150/9; 229/56; 229/62.5; 128/275
[58] Field of Search ................. 150/9, 5, 3, 1; 229/56, 229/62.5, 72; 128/275, 295

[56]  References Cited

U.S. PATENT DOCUMENTS

| | | | |
|---|---|---|---|
| 2,708,067 | 5/1955 | Paton | 150/9 X |
| 3,207,420 | 9/1965 | Kindelan | 229/56 |
| 3,403,715 | 10/1968 | Trudel | 150/9 |
| 3,783,787 | 1/1974 | Thornley et al. | 150/9 X |
| 3,806,025 | 4/1974 | Marshall | 150/9 X |
| 3,823,716 | 7/1974 | Hale | 128/275 |
| 3,888,236 | 6/1975 | Marx | 128/2 F |

FOREIGN PATENT DOCUMENTS

| | | | |
|---|---|---|---|
| 141197 | 5/1951 | Australia | 150/9 |
| 21424 | 5/1883 | Fed. Rep. of Germany | 229/56 |
| 1066427 | 4/1967 | United Kingdom | 150/9 |

Primary Examiner—Joseph Man-fu Moy
Attorney, Agent, or Firm—John A. Dhuey; James R. Henes

[57]  ABSTRACT

A flexible fluid collection bag is described having an upper sampling compartment of predetermined volume and a lower collection compartment partially separated by a heat seal portion, yet remaining in fluid communication with each other. To obtain a fluid sample from the bag, the bag is inverted to fill the sampling compartment, then pivotably held at the connection of the compartments while the collection compartment is returned to its original position. The fluid remaining in the sample compartment then is discharged into a specimen collection container.

9 Claims, 2 Drawing Figures

FLUID COLLECTION RECEPTACLE

This is a continuation, of application Ser. No. 716,308, filed Aug. 20, 1976, now abandoned.

This invention is concerned generally with fluid collection bags. In particular, it is concerned with fluid collection bags used for collection of body fluids from a patient.

Currently utilized collection bags usually are made from flexible sheets of plastic heat-sealed together around their peripheral edges and sealed to an inlet port, which is connected by means of a flexible tube to a patient. It often is necessary to obtain a fluid sample from the bag for laboratory analysis and the like. Generally the bag is inverted and an attempt to release a small amount of fluid is begun. The size of the specimen collection containers often is not greater than about 75 cc. Given the flexible nature of the bag and the small size of the container, it is extremely difficult to fill the container without spilling and consequently contaminating the surrounding area with fluid. Although attempts to minimize these problems have led to installations of improved valves on inlet or outlet lines, results still have not been satisfactory. The primary difficulty is lack of control of the flexible bag when it is filled with fluid.

It has been discovered that a two compartment bag, wherein the two compartments are in fluid communication with each other and the upper compartment is appropriately sized and sited, can solve the above-noted problems.

The invention is best illustrated with reference to the following drawings in which.

Figure 1:
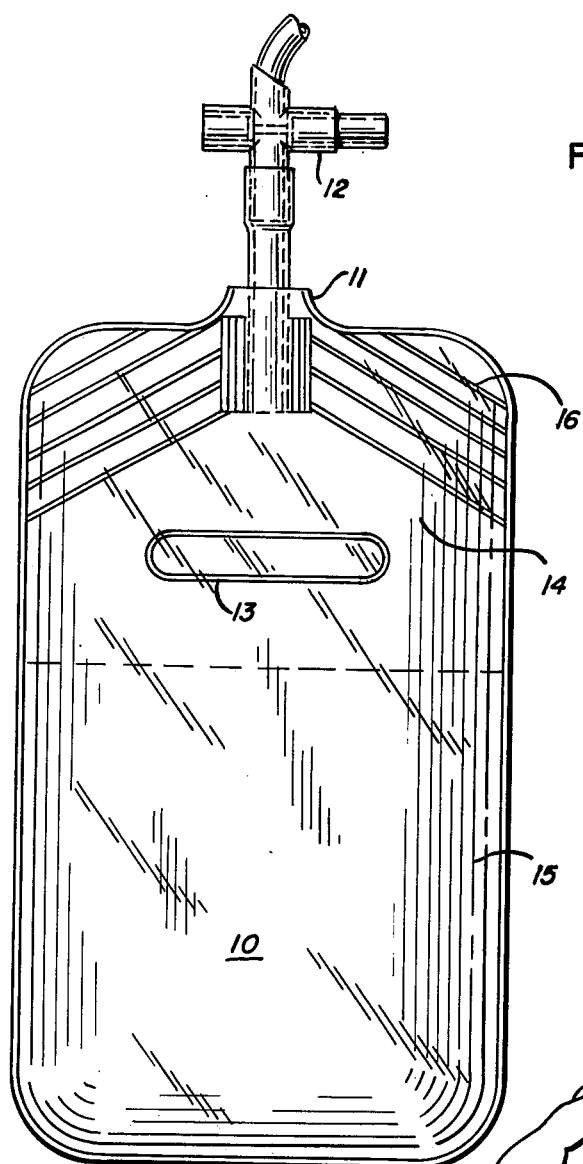
FIG. 1 is a view of the bag in its collection mode.

Urethral drainage bag 10 consists of two heat-sealable plastic sheets sealed about their periphery. An inlet 11 is provided for attachment to a valve 12 which can be connected by a catheter (not shown) to a patient. Bag 10 is largely conventional except in providing an additional heat sealed bar or ring 13, which extends a substantial distance across the width of the bag and yet permits fluid to flow about its ends from the top compartment 14 to the lower compartment 15. Heat seal 13 extends substantially the width of bag 10, but is not coextensive therewith and is heated to form an upper compartment 14 as a specimen trap of a predetermined volume, which is utilized as hereinafter described.

Figure 2:
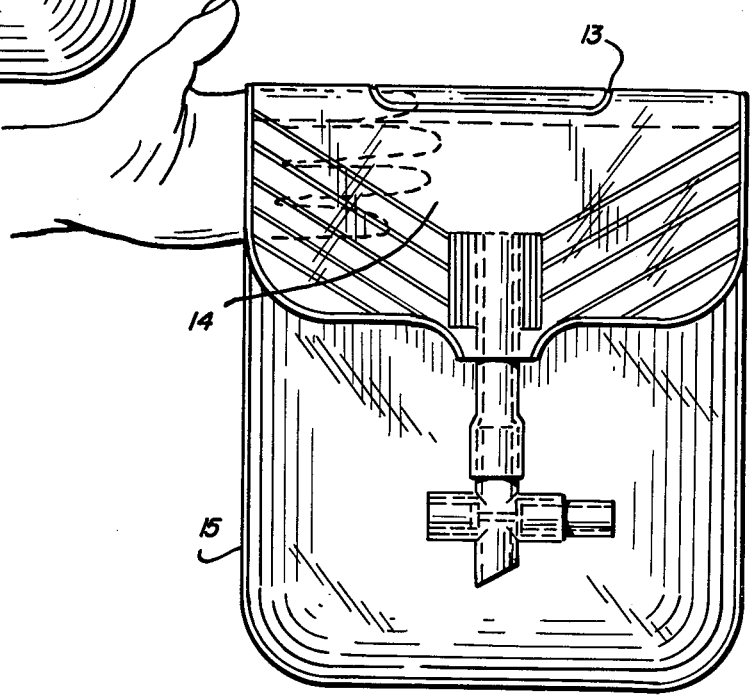
FIG. 2 is a view of the bag in its dispensing mode for dispensing to a specimen container.

After fluid has substantially filled the lower compartment 15, valve 12 is closed and the bag is disconnected from the catheter leading to a patient. At this time a fluid specimen usually is taken so that laboratory tests can be performed. Bag 10 is inverted such that fluid flows into upper compartment 14 from lower compartment 15. Then the bag is held at the bar or ring seal, allowing the bag to drape over the hand, as can be seen most clearly in FIG. 2. The upper specimen compartment 14 is effectively sealed from the remaining portion of bag 10 and retains a predetermined volume of fluid. Valve 12 is opened and the predetermined volume of fluid in compartment 14 is permitted to flow into a specimen container. In practice, the heat-seal bar or ring 13 is placed at a predetermined position such that the volume of compartment 14 is slightly less than that of a standard specimen container, e.g., 30–60 cc. A volume of about 40 cc. is satisfactory for most applications. After the specimen has been taken, valve 12 is closed and bag 10 is disposed of in the usual manner.

Specimen containers can vary in size depending on the nature and number of tests to be performed on the specimen. They may encompass a range of about 10–200 cc., although their volumes generally are about 30–100 cc.

The predetermined volume of upper compartment 14 can be set for the appropriate application. In practice, a specimen container can be provided along with a collection bag having an appropriately sized upper compartment 14.

In an especially preferred embodiment of the device, diagonal heat seal bars 16 are formed in bag 10. Bars 16 generally extend from the outer edges of bag 10 to the area of the inlet 11 to facilitate flow of fluid out of compartment 14 during the dispensing operation. The inclination of bars 16 permits removal of substantially all of the fluid in upper compartment 14.

Collection bag 10 conveniently is manufactured from polyvinylchloride sheet. Typically, such plastic sheeting is about 0.004 to 0.012 inches thick.

The heat sealed peripheral edges of bag 10 and heat seal strips 13 and 16 are formed by conventional methods.

The invention has been described with reference to the drawings but is not meant to be limited thereby. Many variations will be apparent to those skilled in the art without departing from the spirit or scope of this invention.

What is claimed is:

1. In a flexible bag for collection of liquid therein and delivery therefrom of a predetermined volume of collected liquid and having opposing walls of heat-sealable material sealed about their peripheral side, top and bottom edges and a valved port at or near said top edge for flow of liquid into said bag and delivery of a predetermined volume of collected liquid from said bag, said port providing the only opening for flow of liquid into and out of said bag, the improvement which comprises a first seal between said walls extending substantially but not coextensively the width of the bag, said first seal at a predetermined position to create an upper compartment of a predetermined volume in communication with said port and a lower compartment in said bag and to define a passageway between the peripheral side edges of said bag and said first seal whereby liquid can flow thourgh said port and upper compartment to said lower compartment when said bag is in an upright position and said port is open, to collect liquid in said lower compartment and a predetermined volume of collected liquid can flow from said lower compartment to said upper compartment when said bag is in an inverted position and said port is closed, and to define a strip at which said bag can thereafter be folded with said upper compartment inverted and said lower compartment upright and said port closed, to effectively seal said upper and lower compartments, to thereby prevent further flow of collected liquid therebetween and to retain a predetermined volume of collected liquid in said upper compartment for subsequent delivery through said port, and a pair of second seals extending diagonally from the side peripheral edges of said bag at a point below said port and interiorly of said bag to said port whereby said second seals facilitate emptying of said upper compartment when said upper compartment is in an inverted position.

2. The improvement as in claim 1 wherein said first seal is a heat-sealed bar.

3. The improvement as in claim 1 wherein said first seal is a heat-sealed ring.

4. The improvement as in claim 1 wherein the volume of said upper compartment is between about 30–60 cubic centimeters.

5. A flexible bag for collection of liquid therein and delivery therefrom of a predetermined volume of collected liquid comprising two opposed sheets of heat-sealable material, a port formed at one end of said sheet for flow of liquid into said bag and delivery of a predetermined volume of collected liquid from said bag, said sheets being heat-sealed about their peripheral side, top and bottom edges such that said port provides the only opening for flow of liquid into and out of said bag, valve means connected to said port, a first seal between said opposing sheets extending substantially but not coextensively the width of said bag, said first seal at a predetermined position to create an upper compartment of a predetermined volume in communication with said port and a lower compartment in said bag and to define a passageway between the peripheral side edges of said bag and said first seal whereby liquid can flow through said port and upper compartment to said lower compartment to collect in said lower compartment when said bag is in an upright position and said port is open and a predetermined volume of collected liquid can flow from said lower compartment to said upper compartment when said bag is in an inverted position and said port is closed, and to define a strip at which said bag can thereafter be folded with said upper compartment inverted and said lower compartment upright and said port closed, to effectively seal said upper and lower compartments to thereby prevent further flow of collected liquid therebetween and to retain a predetermined volume of collected liquid in said upper compartment for subsequent delivery through said port, and at least one pair of second seals between said opposing sheets extending diagonally from the side peripheral edges of said bag at a point below said port and above said first seal and interiorly of said bag to said port, whereby said second seals facilitate emptying of said upper compartment when said upper compartment is in an inverted position.

6. A collection bag as in claim 5 wherein said second seal is a plurality of pairs of heat-sealed strips.

7. A collection bag as in claim 6 wherein said first seal is a heat-sealed strip.

8. A collection bag as in claim 5 wherein said first and second seals are heat-sealed strips.

9. A collection bag as in claim 5 wherein said first seal is a heat-sealed ring.

* * * * *